(12) United States Patent
Sen

(10) Patent No.: US 8,211,061 B2
(45) Date of Patent: Jul. 3, 2012

(54) INTELLIGENT REMOTE-CONTROLLED PORTABLE INTRAVENOUS INJECTION AND TRANSFUSION SYSTEM

(75) Inventor: Luyi Sen, Shanghai (CN)

(73) Assignee: Sun Medical-Scientific (Shanghai) Co., Ltd, Pudong New Area, Shanghai (CN)

( * ) Notice: Subject to any disclaimer, the term of this patent is extended or adjusted under 35 U.S.C. 154(b) by 682 days.

(21) Appl. No.: 12/446,756

(22) PCT Filed: Oct. 23, 2007

(86) PCT No.: PCT/CN2007/003024
§ 371 (c)(1),
(2), (4) Date: Apr. 23, 2009

(87) PCT Pub. No.: WO2008/052425
PCT Pub. Date: May 8, 2008

(65) Prior Publication Data
US 2010/0030387 A1    Feb. 4, 2010

(30) Foreign Application Priority Data

| Oct. 23, 2006 | (CN) | 2006 1 0117449 |
| Oct. 23, 2006 | (CN) | 2006 1 0117450 |
| Oct. 23, 2006 | (CN) | 2006 1 0117451 |

(51) Int. Cl.
| A61M 1/00 | (2006.01) |
| A61M 37/00 | (2006.01) |
| A61M 31/00 | (2006.01) |
| A61K 9/22 | (2006.01) |
| F04B 49/00 | (2006.01) |

(52) U.S. Cl. ....... 604/151; 604/131; 604/67; 604/890.1; 604/891.1; 417/18; 417/1

(58) Field of Classification Search .................. 604/131, 604/151, 154, 890.1–892.1, 65–67; 417/1, 417/18
See application file for complete search history.

*Primary Examiner* — Kevin C Sirmons
*Assistant Examiner* — Bradley Thomas, Jr.

(57) ABSTRACT

An intelligent remote-controlled portable intravenous injection and transfusion system includes a fluid storage unit (A), a transfusion needle (B), a transfusion tube (C) and a fluid supply driving unit (D). The fluid storage unit (A) is formed by a portable bag (A1) and a fluid storage bag (A2) therein. The fluid supply driving unit (D) includes a peristaltic pump (2), which is provided in a portable flip-shell formed by a lower case (5), an upper cover (6) and a rotational axis (7), and its drive device (1), a power (13), a controller having MSF module and the second wireless signal transmitter/receiver unit. The second wireless signal transmitter/receiver unit is connected to the I/O of the controller. The first wireless signal transmitter/receiver unit is provided in a healthcare monitor room, and connected to the I/O of a computer installed with a controlling software.

10 Claims, 5 Drawing Sheets

INTELLIGENT REMOTE-CONTROLLED PORTABLE INTRAVENOUS INJECTION AND TRANSFUSION SYSTEM

RELATED APPLICATIONS

The present application is related to Chinese Provisional Patent Application serial no. 200610117451.9, 2006210117450.4, 200610117449.1, all of them filed on Oct. 23, 2006, which is incorporated herein by reference and to which priority is claimed pursuant to A61M 5/142, G08C 17/00, H04B7/00, respectively.

BACKGROUND OF THE PRESENT INVENTION

1. Field of Invention

The present invention relates to a medical device, and more particularly to a medical device which is adapted for transfusing a fluid into human bodies.

2. Description of Related Arts

Nowadays, intravenous transfusion is one of the most commonly used methods for clinical first aid and treatment and it is also a commonly used drug-administration therapeutic technique for nursing.

Clinically, it is usually needed for different drugs and patients to select corresponding transfusion speed.

Fast flow rate of infusion can lead to intoxication and even to edema and heart failure. Nevertheless, slow flow rate can lead to insufficient drug administration or the transfusion time being prolonged meaninglessly, which will influence the therapy results and unnecessarily increase the burden of patients and nursing.

In present regular clinical transfusion we are always hanging a transfusion bag or bottle at a certain height (taken veins as a standard), fluid dropping into blood vessels under natural gravity. Besides, we have to observe the level of fluid with eyes, control the drug infusion rate by hand-operated clip. In regular clinical transfusion it is not easy to control the transfusion rate accurately, the workload for healthcare providers is high and the most important is that during the whole transfusion process patients have to keep at a fixed position either sitting or lying without moving or walking freely.

Publication Patent Date is May 24, 2000. The Chinese patent with Publication Number CN 2379139Y published an "automatic transfusion device containing toll bar with location-limited groove", which includes tank, toll bar, monoboard microcomputer, input structure, peristaltic pump and air bubble detection structure. On the tank a front panel was designed with an indented plane corresponding to the toll bar on one side opposite to the peristaltic pump. The transfusion tube was gripped on the upper and lower grip slippers, whose middle part was located in the location-limited groove of the toll bar and was pressed between the location-limited groove and the pump slice of peristaltic pump.

The technical program above introduces a mechanical press-typed injection and transfusion method, which overcomes the deficiency of present gravity-typed transfusion method. However, because the device takes Linear Peristaltic Pump as the pressure source, it makes the volume of the whole device too big, comparatively hulking, poorly movable, unable to meet the need for use under moving condition (such as stretcher-carrying). Meanwhile, the whole device is inconvenient for moving, which still limits the free movement of patients during the transfusion/therapy period.

In addition, Publication Patent Date is May 24, 2000. The Chinese patent with Publication Number CN 2379139Y published a "transfusion pump". This device extracts the signal of fluid drops through electric-optical system, carries out closed-loop system control after the analysis and computation of microcomputer (single-chip computer), drives the peristaltic pump by stepper motor to realize the demand for liquid drop-based transfusion and rapid pressing transfusion and can give an alarm automatically when leakage, blockage or empties occur.

The technical program above introduces a mechanical press-typed injection and transfusion method, which overcomes the deficiency of present gravity-typed transfusion method. But, its control and alarm circuits both take the local control approach by discrete components and all control operations should be completed on the transfusion site, which is not able to relieve the workload of medicinal staff. Furthermore, once all running parameters were set up in programs, the on-site medicinal staff or patients are not able to manually change the setting or make any adjustment according to the particular case of various drugs or patients in time.

Simultaneously, in current techniques, whether when the control device gives an alarm and it needs to inform the medicinal staff to deal with the condition or when patients or their warders find problems during transfusion and need to call for the medicinal staff to deal with the conditions, both need someone to artificially press the alarm button switch installed in the wards and inform the medicinal staff in the control room to deal with the condition. In this case, on one hand there are too many information passing links and the speed is slow; on the other hand, setting large amount of alarm button switches in every ward needs to lay down numerous electrical wires, electric cables and other components, which makes the fee for construction/installation and usage/maintenance too high, and, when the patients alone stays in the ward, esp. for the patients with serious illness, it is almost very difficult or impossible for them themselves to press the switch and give an alarm.

Also, present transfusion device is not able to automatically detect the problems such as whether the drug prescription for transfusion is appropriate for certain patient, whether there are any adverse drug reactions among the drugs prescribed. Thus, the probability for adverse drug reaction occurring is high.

SUMMARY OF THE PRESENT INVENTION

An object of the present invention is to provide an intelligent remote-controlled portable intravenous injection and transfusion system. On the basis of performing the same function, the volume of the driving force transfusion device is decreased greatly and its weight lightened. The whole device owns fine movable performance and portability and patients can carry it with them, which makes it possible for the patients to move freely during the period of transfusion therapy. Besides, the device can dynamically return the real-time running feedback information of the transfusion device to medicinal staff, which facilitates the adjustment of the running parameters for the transfusion device. Also, the device is able to automatically checkout whether the drugs prescribed are correct and proper, which greatly lightens the workload for medicinal staff.

The technical plan for this invention is to provide an intelligent remote-controlled portable intravenous injection and transfusion system, which comprises a fluid storage unit, an infusion needle, an infusion tube connecting the fluid storage unit with the infusion needle, and a fluid supply driving unit provided on the infusion tube, wherein the fluid storage unit comprises a portable bag and a fluid storage bag provided within the portable bag, wherein a belt is provided on the portable bag for fixing on a human body; wherein the fluid supply driving unit comprises a peristaltic pump provided within a portable flip-open cover shell which comprises a lower casing, an upper cover and a rotational axis, a driving arrangement provided within the portable flip-open cover shell, a power supply, and a controlling circuit, wherein the driving arrangement and the peristaltic pump are provided side-by-side within the portable flip-open cover shell, and connected with each other by a transmission arrangement, wherein a controlling arrangement comprises a control circuit provided within an upper cover of the flip-open cover shell, a first parameter input/display unit provided on an outer surface of the upper cover, and a second parameter input/display unit provided on an inner surface of the upper cover, wherein the power supply is connected with the driving arrangement and the controlling arrangement; wherein a section of the infusion tube is fastened at an lateral side of rollers of the peristaltic pump; wherein a first wireless signal transmitter/receiver unit is adapted for being provided in a healthcare monitor room, and connected to an I/O of a computer d installed with a controlling software; wherein a second wireless signal transmitter/receiver unit is provided within the fluid supply driving unit, and connected to an I/O of the controlling arrangement; wherein a mass storage module is provided within the controlling arrangement of the fluid supply driving unit, drugs and pharmacology information of adverse effect, indications, contraindications, delivery methods, dose and calibration, interaction are preset within the mass storage module.

Specially, the fluid storage bag, made of a soft material, has at least one fluid input and/or output tube, wherein the fluid output tube is connected with the infusion needle through the infusion tube; wherein the peristaltic pump is a planetary rotor type peristaltic pump; wherein the driving arrangement is a step motor; wherein the infusion tube clip is provided rotatably on the lateral side of the rollers of the peristaltic pump, wherein a flexible reset member is provided at a rotatable end of the infusion tube clip, a clip pressure regulating member is provided at the other end, wherein the section of the infusion tube is fastened at the lateral side of rollers of the peristaltic pump; wherein the transmission arrangement is gear transmission or belt transmission; wherein the power supply is a rechargeable battery; wherein at least one section of the infusion tube is made of medical grade, non-toxic polypropylene soft plastic, a connector is provided between the infusion tube and the medical grade, non-toxic polypropylene soft plastic tube.

A fastening hook is provided on an outside of the portable flip-open cover shell for fastening on the belt; wherein an infusion tube path or opening is provided on the portable flip-open cover shell, an engaging locker is provided on a lower casing and an upper cover of the portable flip-open cover shell respectively.

The first and second parameter/display unit comprises a touch screen or a keyboard and liquid crystal screen.

The first and second wireless signal/receiver unit is a module circuit of DSP and/or ARM digital signal processor.

Furthermore, the control circuit comprises at least a storage module, a flow rate detection module, an air bubble detection module, a liquid level detection module, a transfusion position detection module, an alarm module, a transfusion status display module, a wireless transmitter/receiver module, a signal transmitter/receiver antenna, a variable speed drive module and/or camera module which are all connected to an I/O of a central control module, respectively; wherein the modules correspondingly link to one another by Data Bus/ Address Bus/Control Bus; wherein the power supply is connected to a power input of the modules; wherein an I/O of the variable speed drive module links to a control end of the peristaltic pump.

The central control module is an MCU microcontroller circuit, MPU universal microprocessor circuit, DSP digital signal processor circuit, PLD programmable logical circuit or CPLD/FPGA large scale programmable logical circuit; wherein the storage module is ROM, RAM, SDRAM, DRAM, FPMDRAM, EDODRAM, EPROM, E$^2$PROM, Flash Memory, Cache Memory, Rambus DRAM, Samsung NAND Card, DDR Moblie or PSRM storage circuit or a combination of the circuits above.

The variable speed drive module is a step motor variable speed circuit; wherein an infra-red detect circuit, or ultrasonic detect circuit is used for the flow rate detecting module, air bubble detecting module, fluid lever detecting module; wherein an acousto optic alarm circuit and voice alarm circuit is used for the alarm module; wherein an LED or LCD display circuit is used for the infusion status display module; wherein a CCD image sensor circuit is used for the camera module.

A computer and I/O peripheral equipment thereof, a control software installed in the computer, the first and second wireless signal transmitter/receiver unit correspondingly and the control circuit of the fluid supply drive unit form a remote-controlled transfusion control system.

Before transfusion, by a way of man-machine conversation or information reading, input related patients' information such as sex, age, weight, a type of drug given, a way and dose of drug administration through the first and second parameter setting/display unit or the computer I/O peripheral equipment; wherein the control circuit of the fluid supply drive unit receives related patients' information and compares with a related drug/pharmacological information preset in the mass memory module, if there is any difference or error between them, the control circuit will give a warning message and refuse carry out a transfusion operation given, if all transfusion parameters conform to preset rules, the control circuit gives an executive command and the fluid supply drive unit starts running according to work parameters input; wherein during an infusion period, the control circuit in the control arrangement conducts periodic or real-time data communication with the computer, monitors a running status of the fluid supply drive unit and uploads a running data through the first and second wireless signal transmitter/receiver unit and an I/O peripheral equipment of the computer; wherein anytime the running status of the fluid supply drive unit are capable of adjusting and/or controlling through the first and second setting/display unit or the I/O peripheral equipment of the computer.

These and other objectives, features, and advantages of the present invention will become apparent from the following detailed description, the accompanying drawings, and the appended claims.

DETAILED DESCRIPTION OF THE PREFERRED EMBODIMENT

Figure 1:
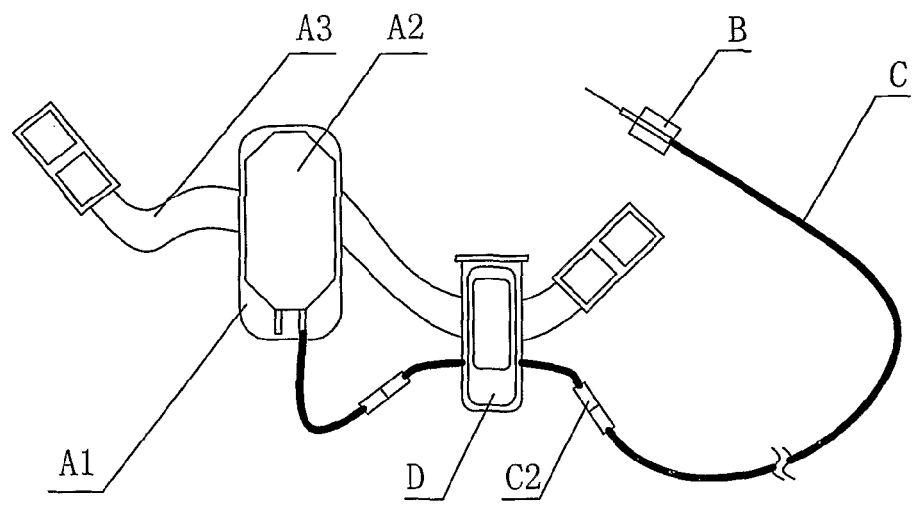
FIG. 1 is the sketch map of the fluid supply drive unit composition in this invention.

Referring to FIG. 1 of the drawings, an intelligent remote-controlled portable intravenous injection and transfusion system according to a preferred embodiment of the present invention is illustrated, in which the system comprises a fluid storage unit A, a infusion needle B, a infusion tube C connecting the fluid storage unit A with the infusion needle B, and a fluid supply driving unit D provided on the infusion tube C.

The fluid storage unit A comprises a portable bag A1 and a fluid storage bag A2 provided within the portable bag A1. A belt A3 is provided on the portable bag A1 for fixing on the human body.

The fluid storage bag, made of a soft material, has at least one fluid input and/or output tube, wherein the fluid output tube is connected with the infusion needle through the infusion tube.

At least one section of the infusion tube is made of medical grade, non-toxic polypropylene soft plastic. A connector C2 is provided between the infusion tube and the medical grade, non-toxic polypropylene soft plastic tube.

A fastening hook is provided on an outside of the fluid supply driving unit to fix on patients. In actual usage, the fluid supply driving unit can be hung on the belt, also can be fixed on the wrist, arm, pocket, or other dresses or clips.

Using this system, patients can early be out of bed for exercise, and get early recovery from the surgery. Elderly patients can manage their daily life, such as go to toilet, by them self during intravenous infusion. Patient can also dress up, out door, do some light exercise or light out door work, in particular, some office work. Children can put on clothes and ply during infusion, then reduce their fear for infusion.

Figure 2:
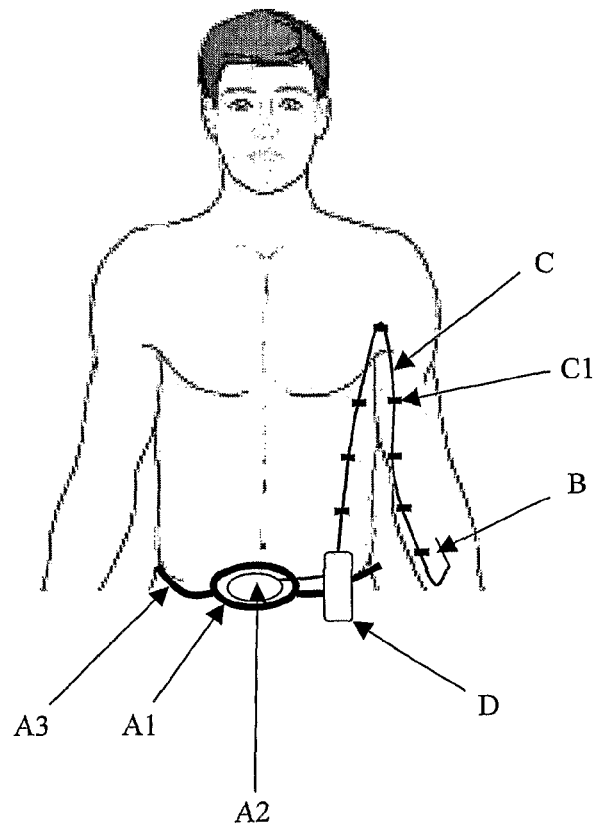
FIG. 2 is the sketch map of its usage method.

In FIG. 2, the belt A3 is used to fix the portable bag A1 and the fluid storage bag A2 provided within the portable bag A1 on a human body.

A plurality of fixing tapes C1 is used to fix the infusion tube C connecting the fluid storage bag and the infusion needle B on the body surface.

Since this system has a portable structure with a small size, light weight, good mobile and portable performance, patients can easily carry it for the freedom of movements to avoid adverse effects caused by long time bedridden and help patients early recovery.

Figure 3:
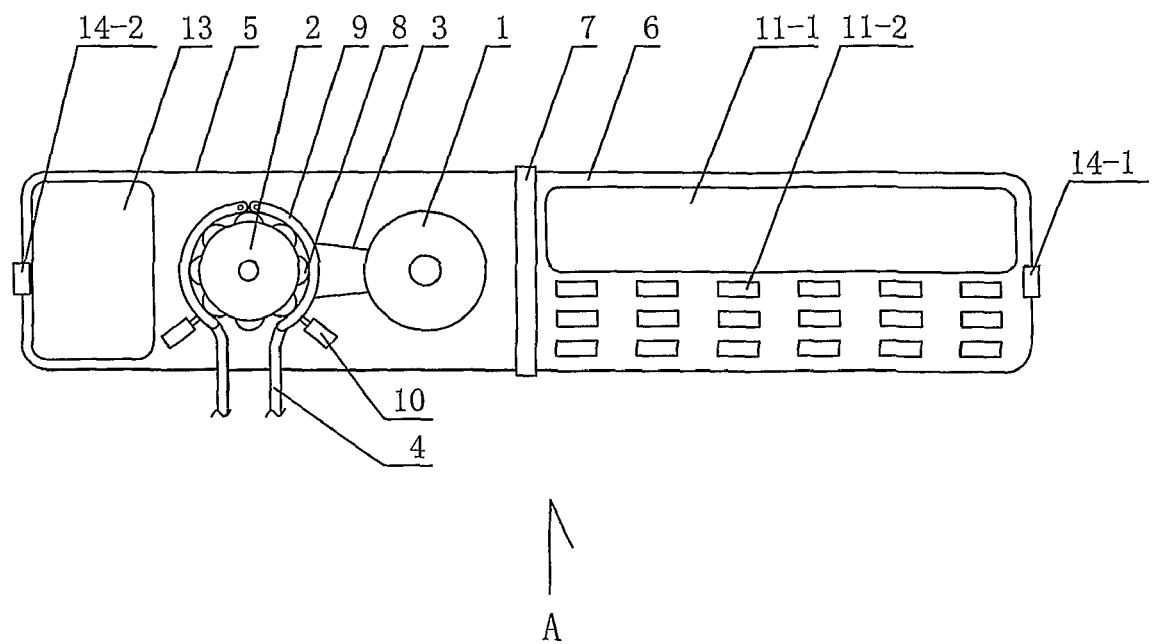
FIG. 3 is the structural sketch map of the fluid supply drive unit.
Figure 4:
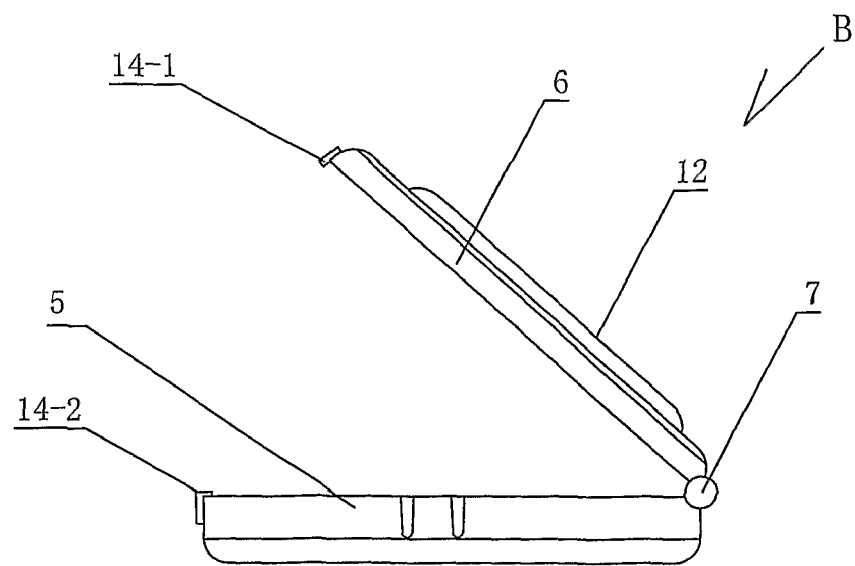
FIG. 4 is the A-oriented view of FIG. 3.
Figure 5:
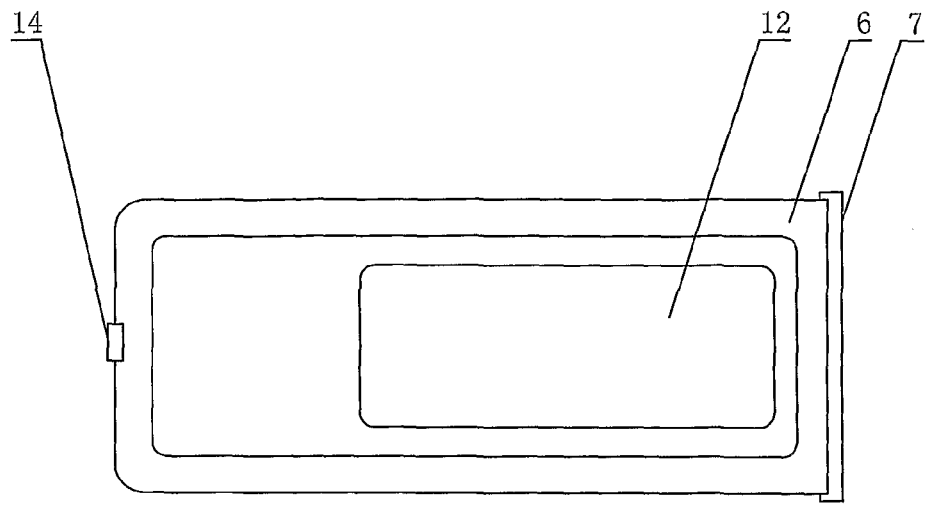
FIG. 5 is the B-oriented view of FIG. 4.

In FIGS. 3-5, the fluid supply driving unit comprises a peristaltic pump 2 provided within a portable flip-open cover shell which comprises a lower casing 5, an upper cover 6 and a rotational axis 7, a driving arrangement 1 provided within the portable flip-open cover shell, a power supply 13, and a controlling circuit.

The peristaltic pump is a planetary rotor type peristaltic pump. The driving arrangement and the peristaltic pump are provided side-by-side within the portable flip-open cover shell, and connected with each other by a transmission arrangement 3. The power supply is connected with the driving arrangement and the controlling circuit.

At least one set arc-shaped infusion tube clip 9 and clip pressure regulating member 10 are provided at an lateral side of the rollers 8 of the peristaltic pump.

The driving arrangement is a step motor.

The transmission arrangement could be either gear transmission or belt transmission. (Only the belt transmission is shown in the figure).

The arc-shaped infusion tube clip is provided rotatably on the lateral side of the rollers of the peristaltic pump.

A flexible reset member (Not shown in Figure) is provided at a rotatable end of the arc-shaped infusion tube clip (an upper end in the figure), the clip pressure regulating member is provided at the other end (a lower end in the figure).

A spring could be used in the flexible reset member. The clip pressure regulating member can be a spring, mechanical or electrical pressure regulating screw set, buckle locker, or positioning pin.

The planet rotor peristaltic pump also called discoid peristaltic pump. This peristaltic pump has an arc-shaped inner peripheral shell, a center rotor, on the edge of the center rotor, axis symmetrically distributed with certain amount rotatable extrude round (so called roller). Transfusion tube is clamped between the peristaltic pump and an arc-shaped inner face shell on the pump. In working state, the step motor driving the center rotor, then the center rotor brings the surrounding c making rounds. The center rotor as the "Star", the extrude rounds as "planet, the extrude rounds making rounds around the center rotor, and also making round around its own axis. Several extrude rounds around the center rotor sequentially extruding (compressing) the infusion tube, that pushes the fluid in the tube flow towards the same direction.

Since using the planet rotor peristaltic pump as the fluid driving force pump, the layout pattern of the infusion tube has been changed (from linear to curve), this change is helpful for further reduce the size of the unit, and the space, created the ideal condition for miniaturization the whole unit for mobile and portable.

The power supply is a rechargeable battery.

The controlling circuit is provided within the upper cover of the flip-open cover shell, an input keyboard 11-2 and a liquid crystal display 11-1 are provided on an inner surface of the upper cover, another display 12 is provided on the outer surface of the upper cover.

The input keyboard and the liquid crystal display provided on the inner surface of the upper cover are used to set/display various parameters for infusion control and the device operation. The display provided on the outer surface of the upper cover is adapted for displaying the infusion operating settings and/or the actual infusion operating parameters/state.

To avoid accidentally changing the setting parameters, or mistakenly touching the input keyboard owing to the accidental open of the flip-open cover shell, an engaging locker 14 is provided.

Figure 6:
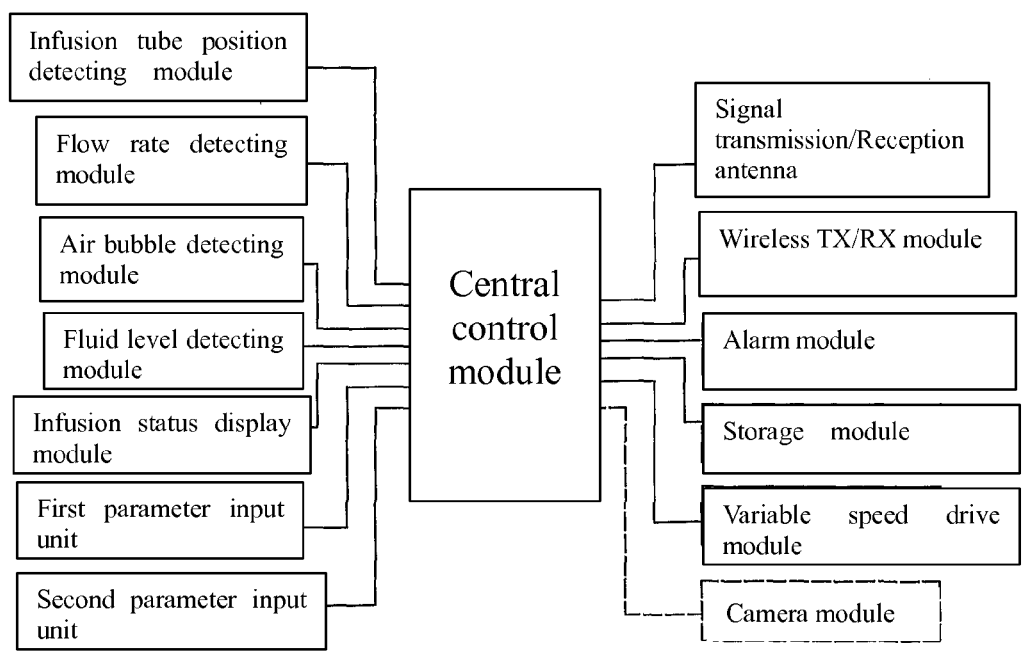
FIG. 6 is the circuit block diagram of the control circuit.

In FIG. 6, the control circuit of this system comprises at least one storage module, a flow rate detecting module, an air bubble detecting module, a fluid lever detecting module, an infusion tube position detecting module, an alarm module, an infusion status display module, a wireless TX/RX module, a signal transmission/reception antenna, a variable speed drive module, and/or a camera module, wherein each of them is connected with a corresponding I/O end of a central control module. Each of the modules described above is connected by a data bus/an address bus/a control bus respectively. The power supply is connected with a power input of each of the modules respectively. An I/O end of the speed drive module is also connected with a corresponding control end of the peristaltic pump.

In the present control circuit, a mass storage module is provided. In this mass storage module, the drug and pharmacology information about the application, adverse effect, indications, contraindications, delivery methods, dose and calibration, interaction of the drugs is provided.

The camera module can also be provided for real-time monitoring the patients.

The center control module k can be a MCU micro-control circuit, a MPU generic microprocessor circuit, a DSP digital signal processor circuit, a PLD programmable logic device circuit or a CPLD/FPGA mass circuit for programmable device. The storage module can be ROM, RAM, SDRAM, DRAM, FPMDRAM, EDODRAM, EPROM, E$^2$PROM, FLASH Memory, Cache Memory, Rambus DRAM, Samsung NAND Card, DDR mobile or PSRM storage circuit or the combinations of circuit described above.

The variable speed drive module is a step motor variable speed circuit. An infra-red detect circuit, or ultrasonic detect circuit can be used for the flow rate detecting module, air bubble detecting module, fluid lever detecting module. An acousto optic alarm circuit and voice alarm circuit can be used for the alarm module. An LED or LCD display circuit can be used for the infusion status display module. A CCD image sensor circuit can be used for the camera module.

A TX/RX integrated circuit chip and corresponding circuit of the cellular phone can be used for the wireless TX/RX module of this system, and the acousto optic alarm circuit and voice alarm circuit in the current mobile phone also can be used for the alarm module in this system. The flow rate detecting module, air bubble detecting module, fluid lever detecting module have been described in the Chinese patent CN 2208935Y, CN2282890Y, CN 2379139Y, CN2574688Y, CN 2810619Y, so they are not further described in here.

Since the modules describe above are available technology, the circuit, structure, working principles and their connections are not be described in here again.

Providing mass storage module could storage enough information and data, such as whole PDR drug directory, could be input into the system, through the software processing to determine the accuracy of drug dose usage, determine the interaction of the drugs, and display the possible adverse effects of the drug. According the patient's information, such as age, weight, sex, etc., the drug dose and can be automatically calibrated, and determine the accuracy of the health care professional's input, giving alarm for the mistake input, and refuse for the wrong operating order. Thus, the malpractice can be reduced.

Figure 7:
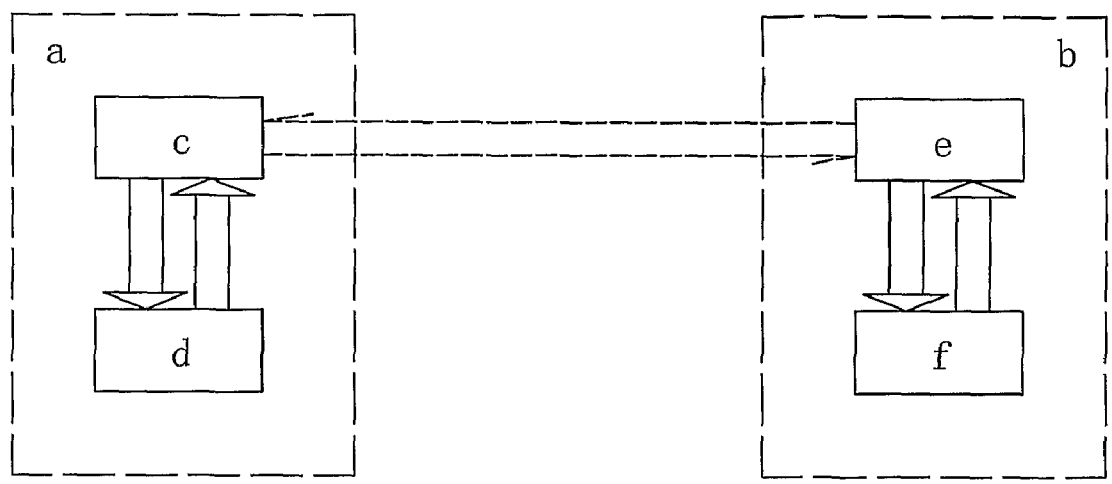
FIG. 7 is the block diagram of the remote-controlled transfusion control system.

In FIG. 7, a first wireless signal transmitter/receiver unit c is provided in a healthcare monitor room, and connected to the I/O of a computer d installed with a controlling software.

Corresponding to the fluid supply driving unit b, there is a second wireless signal transmitter/receiver unit e connected to the I/O of the infusion controller f in the fluid supply driving unit.

Through the setting and the connection described above, the computer and its I/O peripherals, the specific application soft ware loaded in the computer, the correspondent first and second wireless signal transmitter/receiver unit and the infusion control circuit in the c, together formed a wireless infusion control system.

Before the system start work, using person-device communication or information reading receiving method, a first and second parameter input/display units or computer I/O peripheral devices to input the patient's information, such as sex, age, weight, drug name, drug giving method, dose, etc. The control circuit in the fluid supply driving unit receives patient's information, then compares these information to the drug/pharmacology information stored in the mass storage module, if the difference or mistake is find, the control module circuit will give warning signal, refuse process order. If the parameters are all correct, the control circuit will give order to operate, the fluid supply driving unit will start operating fluid infusion according to the working parameters input.

During the infusion, the control circuit in the control module though first and second wireless signal transmitter/receiver unit, the computer I/O peripheral module, communicating with computer for regular or real-time dynamic data communication, monitoring the working states of the fluid supply driving unit, passing the running data to the control unit, through first and second parameter setting/display unit or computer I/O peripheral module, it can regulate or control the fluid supply driving unit operating states anytime.

Figure 8:
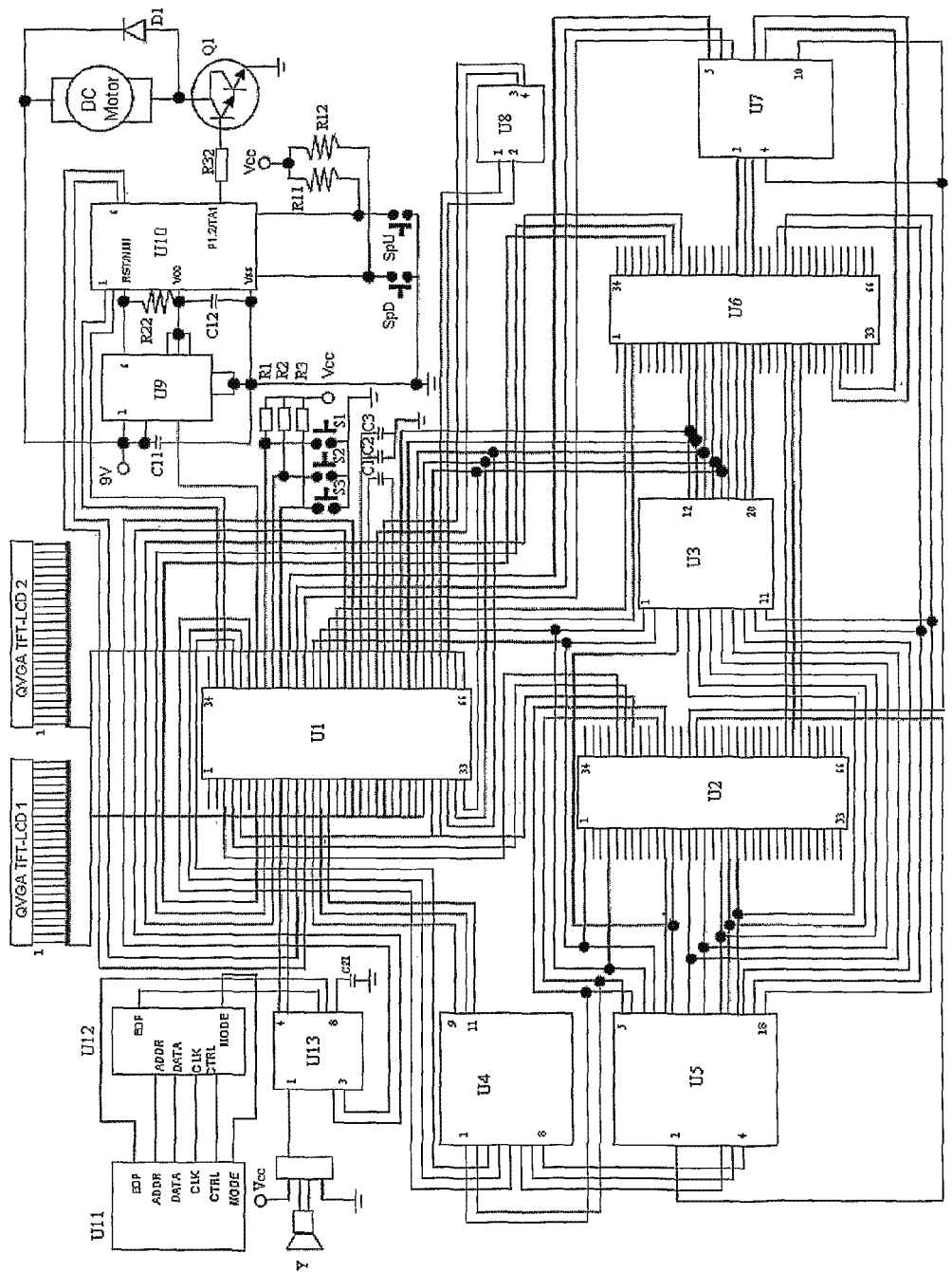
FIG. 8 is the schematic circuit diagram of the control circuit realization.

To help further understand the present invention, FIG. 8 illustrates a circuit diagram as an embodiment of the invention in which the central control module comprises an integrated circuit U1 and a peripheral circuit thereof, the storage module comprises an integrated circuit U2, U3, U5-U8 and their peripheral circuits, the manual set module comprises parameter regulation keys S1-S3 and a touch screen LCD1 and their peripheral circuits, the infusion status display module comprises a touch screen LCD1 and a liquid crystal display LCD2, the variable speed drive module comprises integrated circuits U9, U10, an amplify circuit Q1 and its peripheral circuits, the pressing keys SpD and SpU can regulate a rotating speed of the DC Motor, the alarm module comprises integrated circuits U11-U13, a speaker Y and its peripheral circuit, the second wireless signal transmission/receiving unit comprises a integrated circuit U4 and its peripheral circuit. For simplify the illustration of FIG. 12, the transmission/receiving antenna, camera module that comprises a CCD unit U8 did not shown.

Among each modules described above, the connection is made through data bus/address bus/control bus, respectively. The I/O end of the variable speed drive module is connected with the control input end of the control drive module. The power supply is connected with a power input of each module, respectively.

As can be seen, the circuits described above are currently available in iPod cell phone or cell phones with PDA function except the variable speed drive module. With the specific software, the function of the circuit can be achieved.

Since circuits described above are standard circuits from different integrated circuits manufactures, information about the function of each pin and software definition can all be achieved from the manufactures, so the actual connection of each pin for each integrated circuits is not described here.

Through providing wireless signal transmission/receiving unit and mass storage module, the problems occurred during infusion can be automatically, immodestly discovered and the information can be transferred to the health care professionals on time. This simplified the intermediate link. The investment on the wire alarm system in hospitals, clinics, and home care can be eliminated. This will reduce the cost in long-term for hospitals and patients as well.

As an embodiment of this invention, the integrated circuits are selected as follows:
U1: ARM7 series;
U2: S71WS series;
U3: Samsung NAND Flash 1 Gb;
U4: ST122DSP or STW12000 Series;
U5: Burst NOR 256 Mb;
U6: Moblie SDRAM, DDR, PSRM, DRAM 64-512 Mb;
U7: MCZGH series, GDMCA series;
U8: LZOP373 series;
U9: TPS7 series;
U10: MSP43 series;
U11: W5130 series;
U12: W55F series;
U13: W5810 series.

Modules described above not only limited in the listed model, it will be perfectly fine for using the modules has the same or similar function to replace them. This is obvious for the technical personnel in this field, and does not need any creative work.

However, this did not means this invention is only limited in using integrated modules described above, indeed modules with the same or similar function, or other series integrated modules with the same or similar function can also achieving the technical effects of this invention, their logical connective relations and/or actual circuit connections are also included in the scope of the claim of the present invention.

The embodiment is only used for explain and description of the present invention, it should not be used for the limitation on the scope of claimed invention.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements (such as system, unit, modules, circuit or components) of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

APPLICATION

In the present invention, the infusion pump using portable design with small size and light weight, mobile, easy for patient carry. This design revolutionized the traditional infusion pump that is heavy hanging unit, largely limits the patients' movement. The control system using matured wireless IT, control strategy, the circuit is stable and reliable, low maintenance, relatively low coast, and easy to be accepted by the hospital. This system can accurately set, detect and control the infusion fluid amount and speed, can real-time report the infusion states to the healthcare professionals, achieved intelligent wireless control, easy to manage, significantly reduced the working load of health professionals, reduce the malpractice, and can be used in many fields.

What is claimed is:

1. An intelligent remote-controlled portable intravenous injection and transfusion system, comprising a fluid storage unit, an infusion needle, an infusion tube connecting said fluid storage unit with said infusion needle, and a fluid supply driving unit provided on said infusion tube,
   wherein said fluid storage unit comprises a portable bag and a fluid storage bag provided within said portable bag, wherein a belt is provided on said portable bag for fixing on a human body;
   wherein said fluid supply driving unit comprises a peristaltic pump provided within a portable flip-open cover shell which comprises a lower casing, an upper cover and a rotational axis, a driving arrangement provided within said portable flip-open cover shell, a power supply, and a controlling circuit, wherein said driving arrangement and said peristaltic pump are provided side-by-side within said portable flip-open cover shell, and connected with each other by a transmission arrangement, wherein a controlling arrangement comprises a control circuit provided within an upper cover of said flip-open cover shell, a first parameter input/display unit provided on an outer surface of said upper cover, and a second parameter input/display unit provided on an inner surface of said upper cover, wherein said power supply is connected with said driving arrangement and said controlling arrangement;
   wherein a section of said infusion tube is fastened at an lateral side of rollers of said peristaltic pump;
   wherein a first wireless signal transmitter/receiver unit is adapted for being provided in a healthcare monitor room, and connected to an I/O of a computer d installed with a controlling software;
   wherein a second wireless signal transmitter/receiver unit is provided within said fluid supply driving unit, and connected to an I/O of said controlling arrangement;
   wherein a mass storage module is provided within said controlling arrangement of said fluid supply driving unit, drugs and pharmacology information of adverse effect, indications, contraindications, delivery methods, dose and calibration, interaction are preset within said mass storage module.

2. The intelligent remote-controlled portable intravenous injection and transfusion system, as recited in claim 1, wherein said fluid storage bag, made of a soft material, has at least one fluid input and/or output tube, wherein said fluid output tube is connected with said infusion needle through said infusion tube;
   wherein said peristaltic pump is a planetary rotor type peristaltic pump;
   wherein said driving arrangement is a step motor;

wherein an infusion tube clip is provided rotatably on said lateral side of said rollers of said peristaltic pump, wherein a flexible reset member is provided at a rotatable end of said infusion tube clip, a clip pressure regulating member is provided at the other end, wherein said section of said infusion tube is fastened at said lateral side of rollers of said peristaltic pump;

wherein said transmission arrangement is gear transmission or belt transmission;

wherein said power supply is a rechargeable battery;

wherein at least one section of said infusion tube is made of medical grade, non-toxic polypropylene soft plastic, a connector is provided between said infusion tube and said medical grade, non-toxic polypropylene soft plastic tube.

3. The intelligent remote-controlled portable intravenous injection and transfusion system, as recited in claim 1, wherein a fastening hook is provided on an outside of said portable flip-open cover shell for fastening on said belt; wherein an infusion tube path or opening is provided on said portable flip-open cover shell, an engaging locker is provided on a lower casing and an upper cover of said portable flip-open cover shell respectively.

4. The intelligent remote-controlled portable intravenous injection and transfusion system, as recited in claim 1, wherein said first and second parameter/display unit comprises a touch screen or a keyboard and liquid crystal screen.

5. The intelligent remote-controlled portable intravenous injection and transfusion system, as recited in claim 1, wherein said first and second wireless signal/receiver unit is a module circuit of DSP and/or ARM digital signal processor.

6. The intelligent remote-controlled portable intravenous injection and transfusion system, as recited in claim 1, wherein said control circuit comprises at least a storage module, a flow rate detection module, an air bubble detection module, a liquid level detection module, a transfusion position detection module, an alarm module, a transfusion status display module, a wireless transmitter/receiver module, a signal transmitter/receiver antenna, a variable speed drive module and/or camera module which are all connected to an I/O of a central control module, respectively;

wherein said modules correspondingly link to one another by a Data Bus/Address Bus/Control Bus;

wherein said power supply is connected to a power input of said modules;

wherein an I/O of said variable speed drive module links to a control end of said peristaltic pump.

7. The intelligent remote-controlled portable intravenous injection and transfusion system, as recited in claim 6, wherein said central control module is an MCU microcontroller circuit, MPU universal microprocessor circuit, DSP digital signal processor circuit, PLD programmable logical circuit or CPLD/FPGA large scale programmable logical circuit; wherein said storage module is a ROM, RAM, SDRAM, DRAM, FPMDRAM, EDODRAM, EPROM, $E^2$PROM, Flash Memory, Cache Memory, Rambus DRAM, Samsung NAND Card, DDR Moblie or PSRM storage circuit or a combination of said circuits above.

8. The intelligent remote-controlled portable intravenous injection and transfusion system, as recited in claim 6, wherein said variable speed drive module is a step motor variable speed circuit; wherein an infra-red detect circuit, or ultrasonic detect circuit is used for said flow rate detecting module, air bubble detecting module, fluid lever detecting module; wherein an acousto optic alarm circuit and voice alarm circuit is used for said alarm module; wherein an LED or LCD display circuit is used for said infusion status display module; wherein a CCD image sensor circuit is used for said camera module.

9. The intelligent remote-controlled portable intravenous injection and transfusion system, as recited in claim 1, wherein a computer and I/O peripheral equipment thereof, a control software installed in said computer, said first and second wireless signal transmitter/receiver unit correspondingly and said control circuit of said fluid supply drive unit form a remote-controlled transfusion control system.

10. The intelligent remote-controlled portable intravenous injection and transfusion system, as recited in claim 9, wherein before transfusion, by a way of man-machine conversation or information reading, input related patients' information such as sex, age, weight, a type of drug given, a way and dose of drug administration through said first and second parameter setting/display units or said computer I/O peripheral equipment;

wherein said control circuit of said fluid supply drive unit receives related patients' information and compares with a related drug/pharmacological information preset in said mass memory module, if there is any difference or error between them, said control circuit will give a warning message and refuse carry out a transfusion operation given, if all transfusion parameters conform to preset rules, said control circuit gives an executive command and said fluid supply drive unit starts running according to work parameters input;

wherein during an infusion period, said control circuit in said control arrangement conducts periodic or real-time data communication with said computer, monitors a running status of said fluid supply drive unit and uploads a running data through said first and second wireless signal transmitter/receiver unit and an I/O peripheral equipment of said computer;

wherein anytime said running status of said fluid supply drive unit are capable of adjusting and/or controlling through said first and second setting/display unit or said I/O peripheral equipment of said computer.

* * * * *